US010806663B2

(12) United States Patent
Fallas

(10) Patent No.: US 10,806,663 B2
(45) Date of Patent: Oct. 20, 2020

(54) SEXUAL STIMULATION DEVICE WITH MULTIPLE PHALLIC ELEMENTS

(71) Applicant: Robert Fallas, Huntington Station, NY (US)

(72) Inventor: Robert Fallas, Huntington Station, NY (US)

( * ) Notice: Subject to any disclaimer, the term of this patent is extended or adjusted under 35 U.S.C. 154(b) by 31 days.

(21) Appl. No.: 16/000,422

(22) Filed: Jun. 5, 2018

(65) Prior Publication Data

US 2019/0365599 A1 Dec. 5, 2019

(51) Int. Cl.
*A61F 5/00* (2006.01)
*A61H 19/00* (2006.01)

(52) U.S. Cl.
CPC ............. *A61H 19/44* (2013.01); *A61H 19/30* (2013.01); *A61H 19/50* (2013.01)

(58) Field of Classification Search
CPC ........ A61H 19/00; A61H 19/30; A61H 19/40; A61H 19/44; A61H 19/50; A61H 21/00
USPC ...................................................... 600/38–41
See application file for complete search history.

(56) References Cited

U.S. PATENT DOCUMENTS

| | | | |
|---|---|---|---|
| 5,690,604 A | 11/1997 | Barnett | |
| 6,132,366 A * | 10/2000 | Ritchie | A61H 19/34 600/38 |
| D750,796 S * | 3/2016 | Bains | D24/214 |
| 2014/0358045 A1 | 12/2014 | Toto | |
| 2014/0378758 A1* | 12/2014 | Mankin | A61H 19/44 600/38 |
| 2017/0119617 A1 | 5/2017 | Bargowski | |

FOREIGN PATENT DOCUMENTS

| | | |
|---|---|---|
| CH | 688262 A5 | 12/2017 |
| KR | 101713448 B1 | 3/2017 |
| WO | WO03099189 A1 | 12/2013 |

* cited by examiner

*Primary Examiner* — John P Lacyk
(74) *Attorney, Agent, or Firm* — Gloria Tsui-Yip, Esq.; Gottlieb, Rackman & Reisman, P.C.

(57) ABSTRACT

A sexual stimulation device with a base having an upper portion and a lower portion, and a plurality of phallic elements attached to the lower portion of the base. Each phallic element has a body with a distal end pointing in a generally upward direction. The phallic element may be removably attachable to the base and may be movable relative to the base. The phallic element may also be telescopically extendable and rotatable. The sexual stimulation device may be mountable to a sturdy support via an arm extension.

20 Claims, 8 Drawing Sheets

SEXUAL STIMULATION DEVICE WITH MULTIPLE PHALLIC ELEMENTS

FIELD OF THE INVENTION

This invention relates to a sexual stimulation device. In particular, an improved sexual stimulation device having multiple phallic elements.

BACKGROUND OF THE INVENTION

Sex toys and erotic sexual stimulation devices consist of various shapes and sizes that attempt to arouse or sexually stimulate the user. Sexual stimulation device typically includes a phallic element to mimic the shape and size of a human penis and is used in such a way to simulate sexual activity. The device may include a dildo and/or vibrator. Dildos have set backs in that they usually only contain one phallic element having one shape and/or size. Therefore, a user is limited to the shape, size, and vibration of that device. If a user desires different shapes, sizes and/or features, multiple dildos are required.

Additionally, most sexual stimulation devices require that a user hold the device and/or have a partner hold the device during use. However, during sexual activity, it is desirable to have both hands free for other activity and/or uses.

Therefore, there is a need for a sexual stimulation device that has multiple phallic elements with various shapes and sizes that can be used without user assistance by being mounted and provides additional pleasure to a user.

SUMMARY OF THE INVENTION

The present invention is a sexual stimulation device with multiple phallic elements that provide convenience and added pleasure to a user without the need for multiple, separate, dildos.

The sexual stimulation device of the present invention takes the shape of an octopus, with each tentacle of the octopus being a separate dildo extending from the octopus mantle base. Each dildo may have a different shape, size, color, texture, type, feature, and made of different material, etc. Each dildo may be removably detachable from the base and may be movably positioned with respect to the base at different angles and positions. Each dildo may be telescopically extendable from the base.

The sexual stimulation device may be removably mountable to a wall or bed frame via an arm extension. One end of the arm extension is removably attachable to the mantel base. A bracket may be fixedly positioned on a wall or bed frame and the other end of the arm extension is removably attachable to the bracket. Alternatively, the other end of the arm extension may have a clamp element for fastening directly to a bed frame.

BRIEF DESCRIPTION OF THE DRAWINGS

Preferred embodiments of the present invention have been chosen for purposes of illustration and description and are shown in the accompanying drawings, which are not necessarily to scale, forming a part of the specification wherein.

DETAILED DESCRIPTION OF THE PREFERRED EMBODIMENTS

With reference to the drawings, wherein the same reference number indicates the same element throughout, there is shown in FIGS. 1 to 4 the sexual stimulation device 10 of the present invention. The sexual stimulation device 10 of the present invention has an octopus shape with a mantle base 100 and a plurality of tentacles 200 (200*a,* 200*b,* etc.) extending therefrom. Although eight (8) tentacles 200 are shown to resemble an octopus, more or less tentacles 200 can be used.

Figure 1:
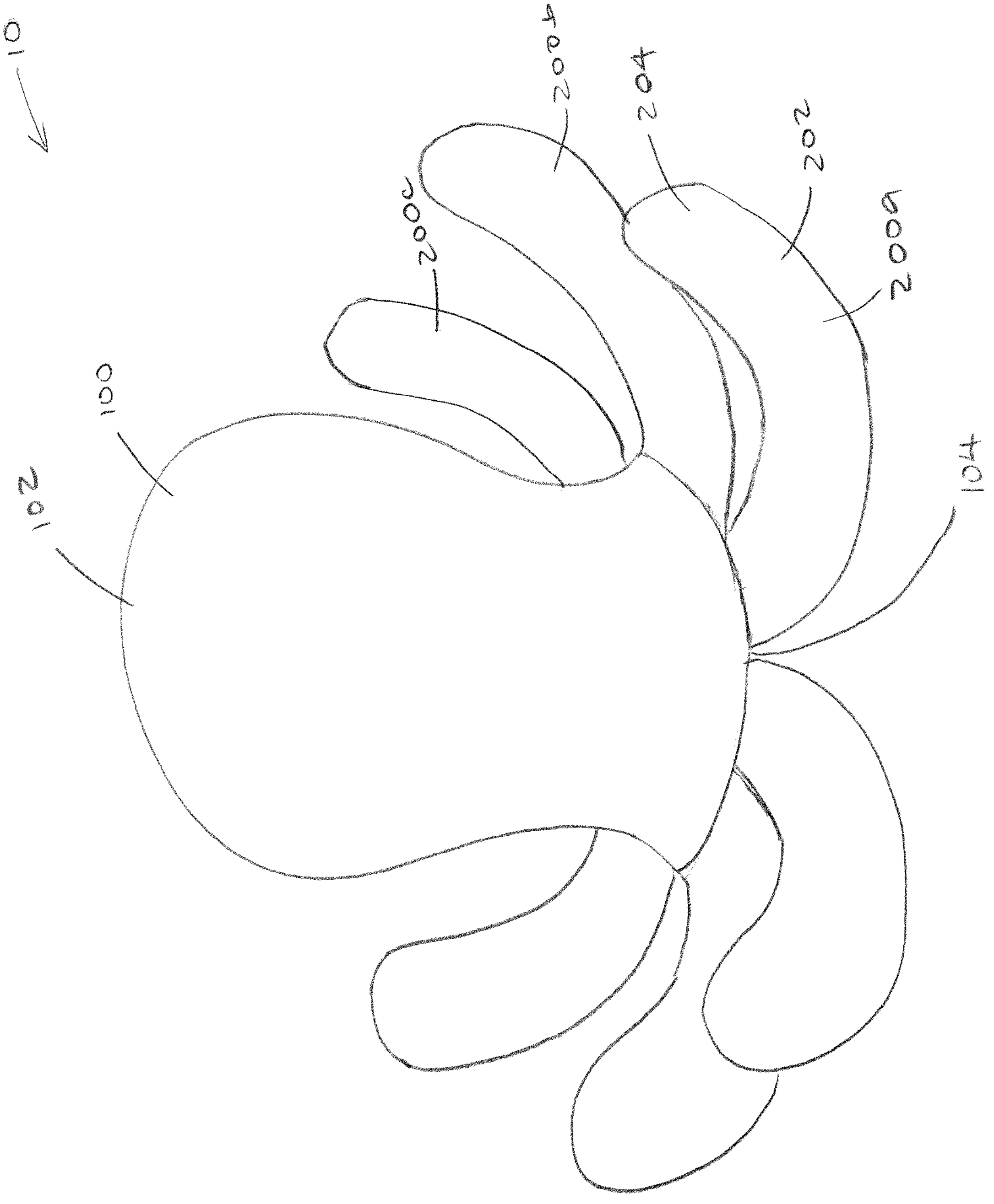
FIG. 1 is a perspective view of the sexual stimulation device of the present invention.
Figure 2:
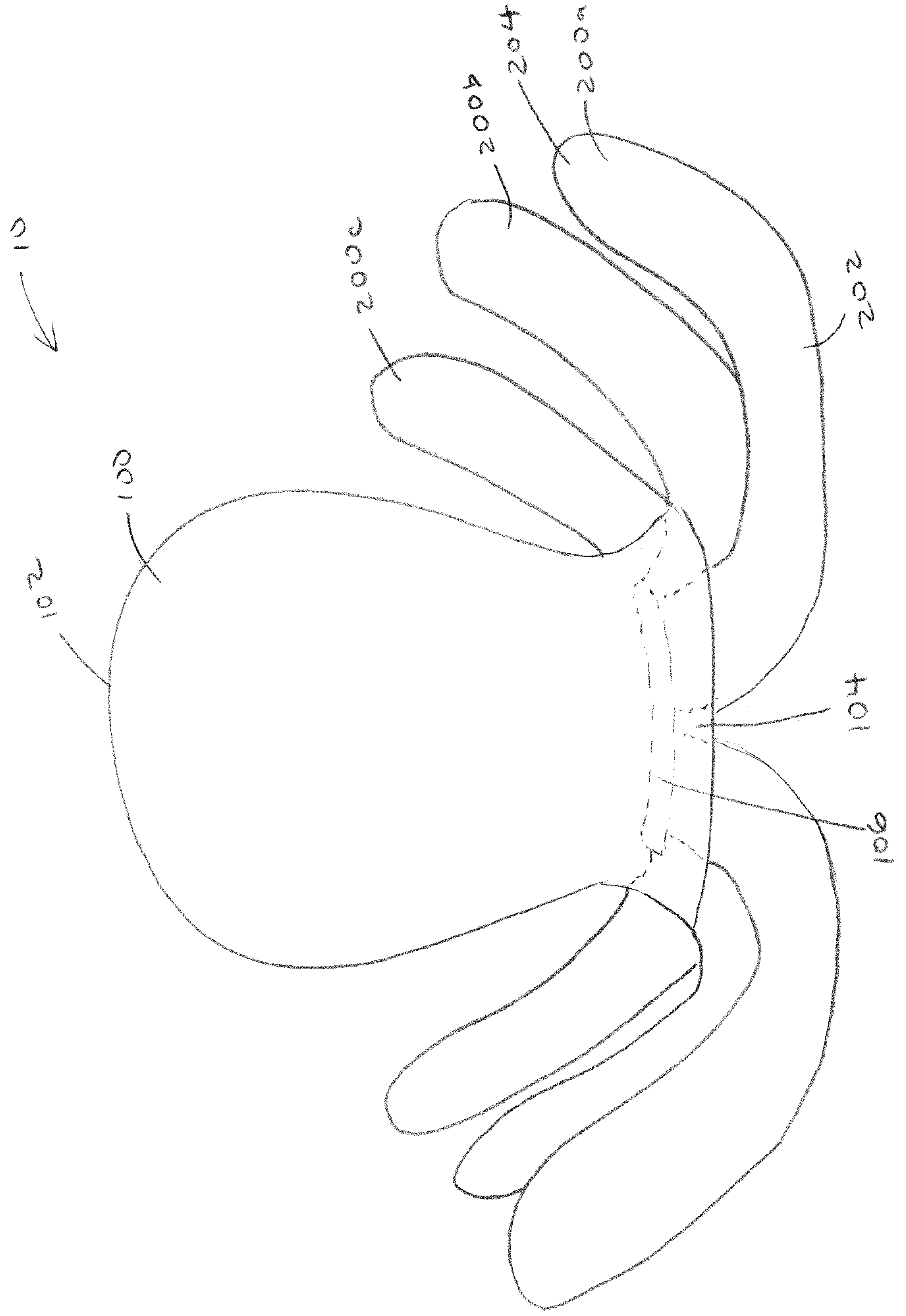
FIG. 2 is a front elevational view of the sexual stimulation device of the present invention.
Figure 3:
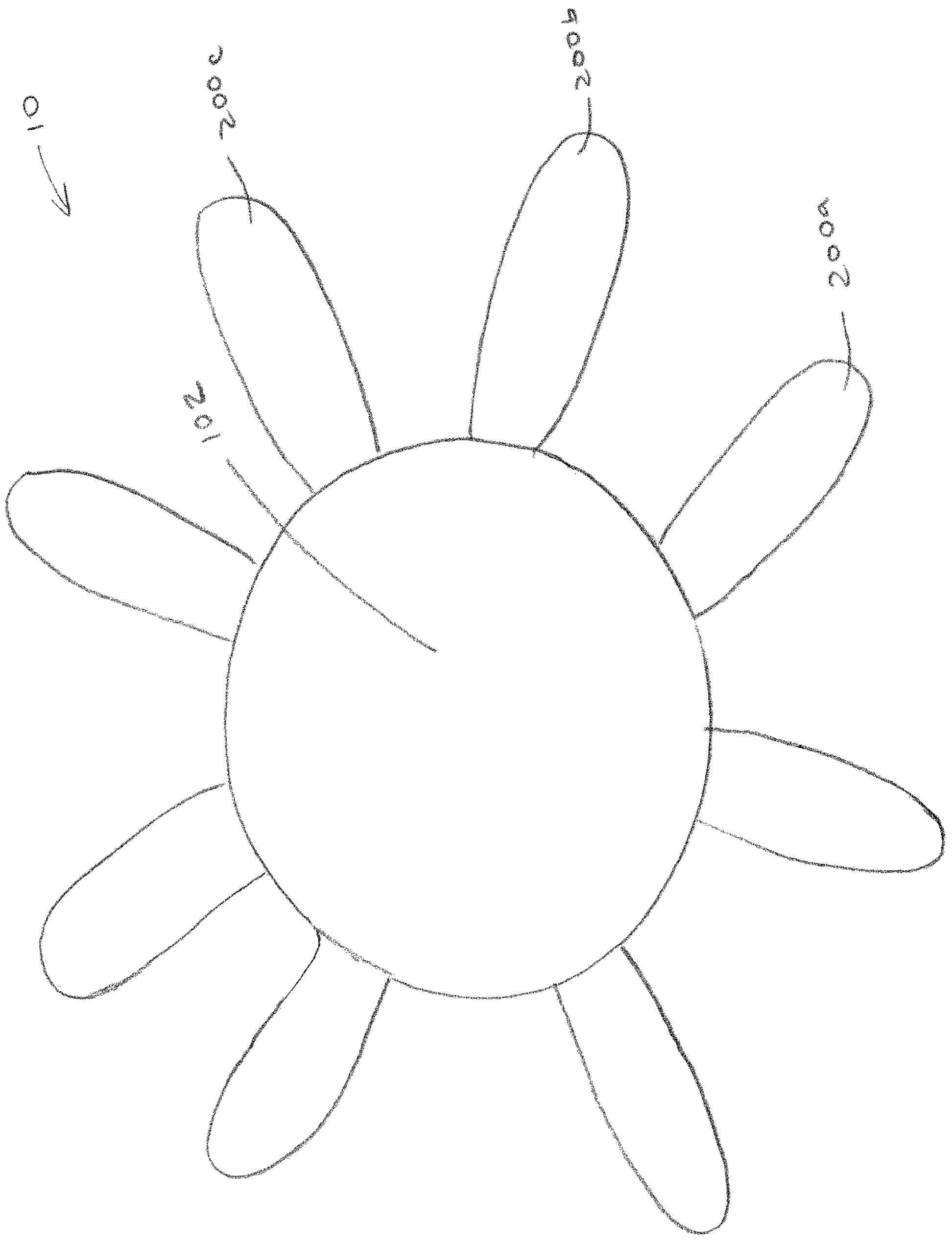
FIG. 3 is a top plan view of the sexual stimulation device of the present invention.
Figure 4:
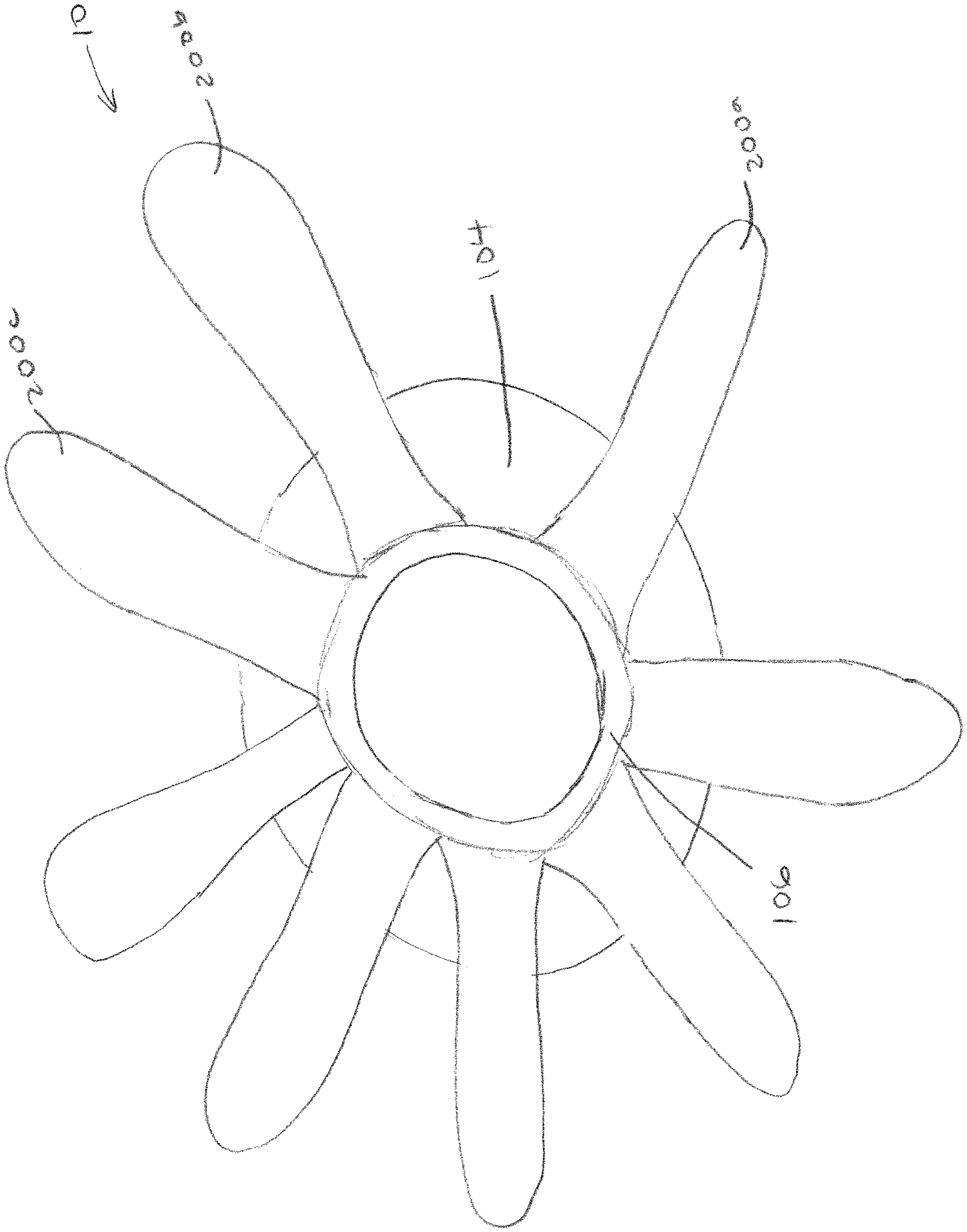
FIG. 4 is a bottom plan view of the sexual stimulation device of the present invention.

The mantle base 100 has a upper bulbous portion 102 and a lower concave portion 104. Each tentacle 200 extends from the lower concave portion 104 and has a curved body 202 resulting in a distal end 204 that points generally in an upward direction. Each tentacle 200 may be fixedly attached to the lower concave portion 104 of the mantle base 100. Alternatively, each tentacle 200 may be movably attached to a track 106 on the lower concave portion 104 of the mantle base 100. For a generally circular track 106 as shown in FIG. 4, the tentacles 200 may be movably attached to provide spaces between adjacent tentacles 200 as desired (e.g. 200*a* and 200*b* in FIG. 4). The tentacles 200 may also be evenly distributed on the track 106 (not shown) as desired by a user.

Figure 5A:
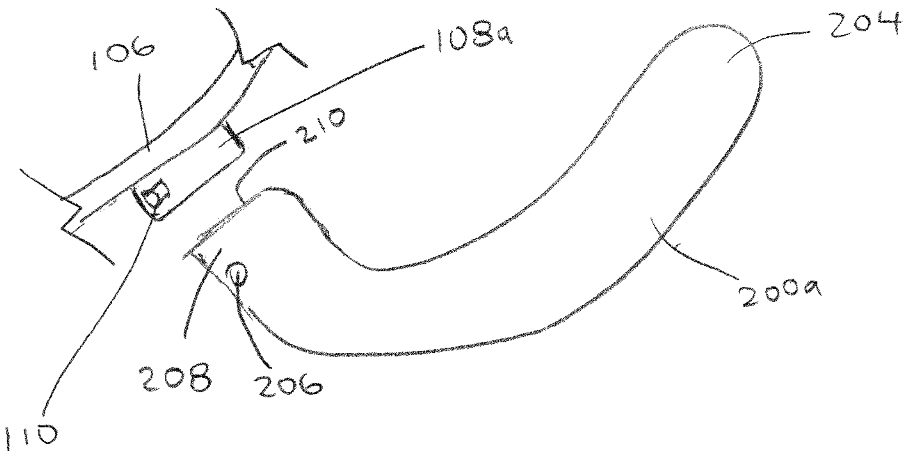
FIGS. 5A and 5B illustrate various methods of attaching the phallic element.
Figure 5B:
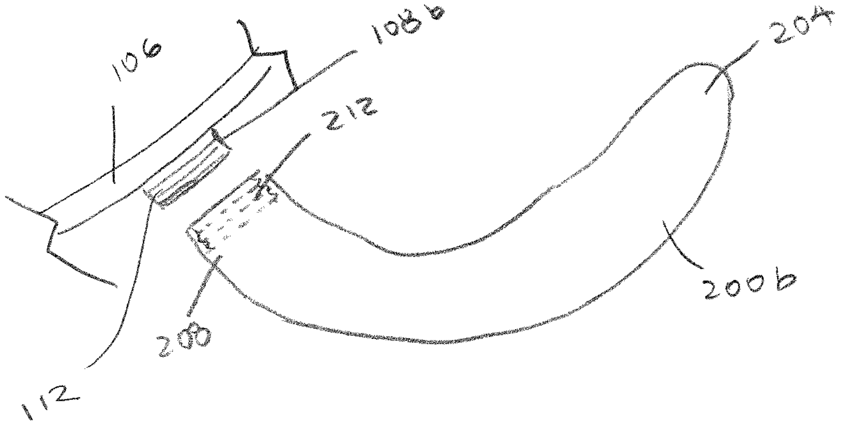

Each tentacle 200 can also be removably attached to the lower concave portion 104 of the mantle base 100 as illustrated in FIGS. 5A and 5B. FIG. 5A shows a hole 206 near the proximal end 208 of tentacle 200*a.* The proximal end 208 of tentacle 200*a* has a cavity 210 that correspondingly receives a mounting element 108*a.* The mounting element 108*a* is attached to the track 106 and has a corresponding spring-loaded detent 110 that fits into the hole 206 when tentacle 200*a* is attached to the mounting element 108*a.* To remove the tentacle 200*a* from the mounting element 108*a,* the user can depress the detent 110 such that it clears the hole 206 and tentacle 200*a* can be pulled away from the mounting element 108*a.* To mount the tentacle 200*a* onto the mounting element 108*a,* the user can depress the detent 110 to fit the mounting element 108*a* in the cavity 210 at the proximal end 208. Tentacle 200*a* is locked onto mounting element 108 when the detent 110 is extended through the hole 206. Although one set of hole 206 and detent 110 is shown, a plurality of sets of hole 206 and detent 100 can be provided at the proximal end 208 of tentacle 200*a* and mounting element 108*a,* respectively. Depending on the positions of the set of hole 206 and detent 110 on the proximal end 208 of tentacle 200*a* and mounting element 108*a,* respectively, the tentacle 200*a* may be attached at different rotational angles relative to the mantel base 100.

FIG. 5B shows a tentacle 200*b* with a proximal end 208 having an internal thread 212. The mounting element 108*b* attached to track 106 has corresponding external thread 112 for receiving the internal thread 212. To attach or remove the tentacle 200*b* from the mounting element 108*b,* the user can rotate the tentacle 200*b* relative to the mounting element 108*b* in a clockwise or counter-clockwise direction, respectively. A stop (not shown) may be provided to prevent the over-rotation of the tentacle 200*b* relative to the mounting element 108*b* such that the tentacle 200*b* rests at a desired angle with the distal end 204 pointing in a generally upward direction. Other than the hole 206—detent 110 attachment of FIG. 5A and the internal thread 212—external thread 112 attachment of FIG. 4B, other structures of attaching the tentacle 200 to the mantle base 100 known by one skilled in the art can be used, such as bayonet mount, a push-pull connector, snap fit, friction hold, etc.

Figure 6A:
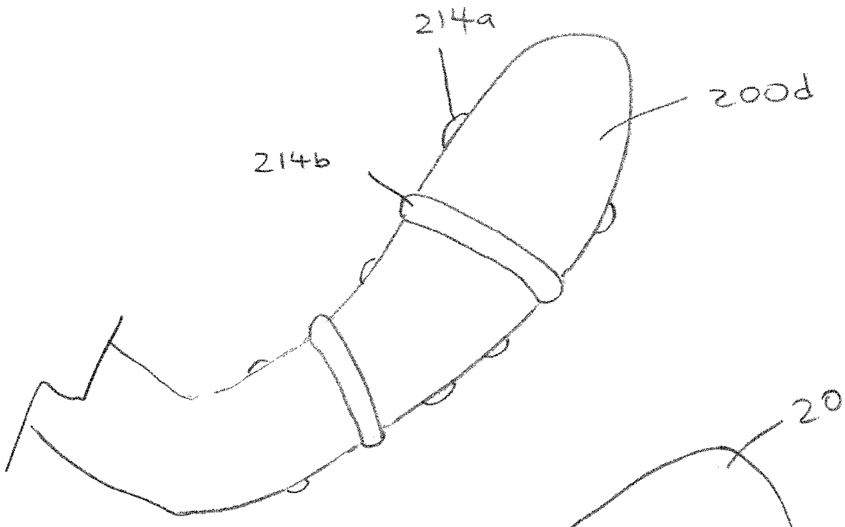
FIGS. 6A-6C illustrate different shapes, styles, and features of phallic elements.
Figure 6B:
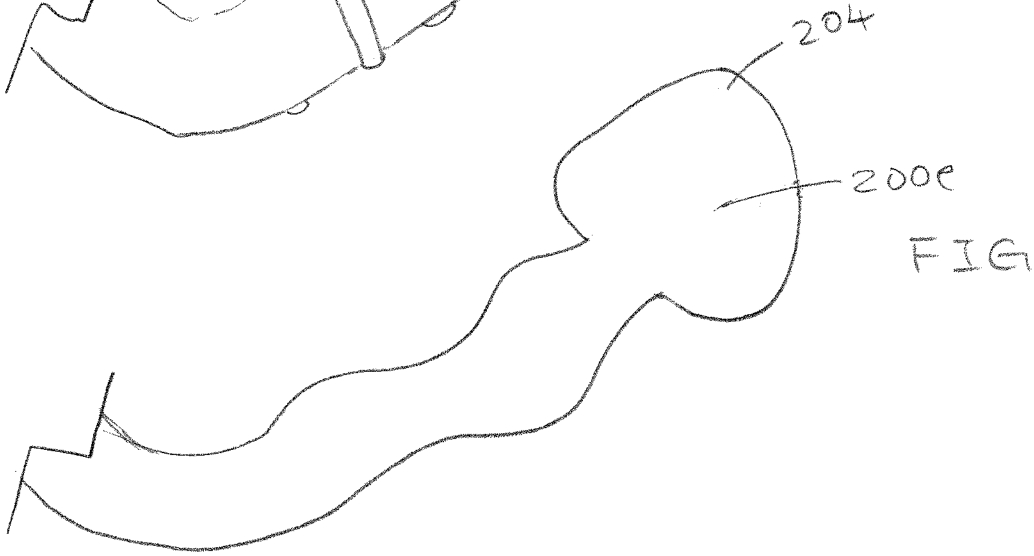
Figure 6C:
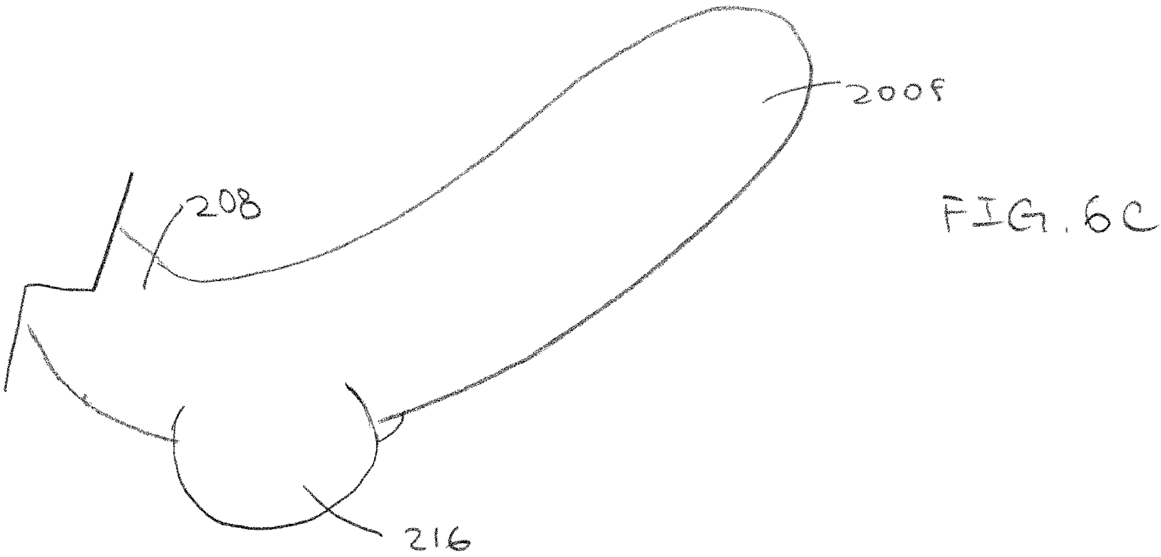

Although each tentacle 200 in FIGS. 1 to 5 is shown as generally cylindrical with a curved body 202, each tentacle 200 is a phallic element such as a dildo. Each tentacle/dildo 200 of the sexual stimulation device 10 of the present invention can have any shape, size, color, texture or feature and can be made of any material known to one skilled in the art. FIGS. 6A to 6C illustrate different shapes, styles and features of tentacle 200. FIG. 6A shows a dildo 200*d* with small bumps 214*a* or ridges 214*b* on the surface. FIG. 6B shows a dildo 200*e* with a wavy contour surface and an enlarged distal end 204. FIG. 6C shows a dildo 200*f* with testicles 216 near the proximal end 208. Other extensions or protrusions similar to testicles 216 can be provided on dildo 200 to provide additional sexual stimulation to the user. Tentacle 200 can be made of silicone, rubber, or other appropriate material known to one skilled in the art. Tentacle 200 can be limp, flexible, firm, inflatable, or bendable to various positions. Tentacle 200 can be solid or hollow. Tentacle 200 can include a vibrator that is battery-operated with the battery located either within the tentacle 200 or at the mantle base 100. A vibrating tentacle 200 can also be powered by alternating current via a power cord extending from the mantle base 100. Tentacle 200 can incorporate a heating element therein to warm up the tentacle 200 to improve enjoyment of the sexual stimulation.

Figure 7A:
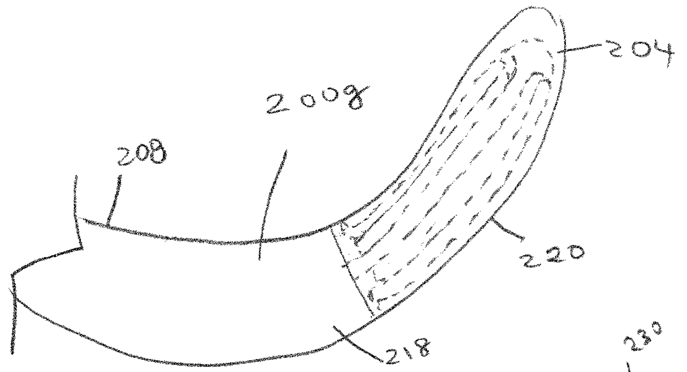
FIGS. 7A-7C illustrate a telescopic and rotatable feature of the phallic element.
Figure 7B:
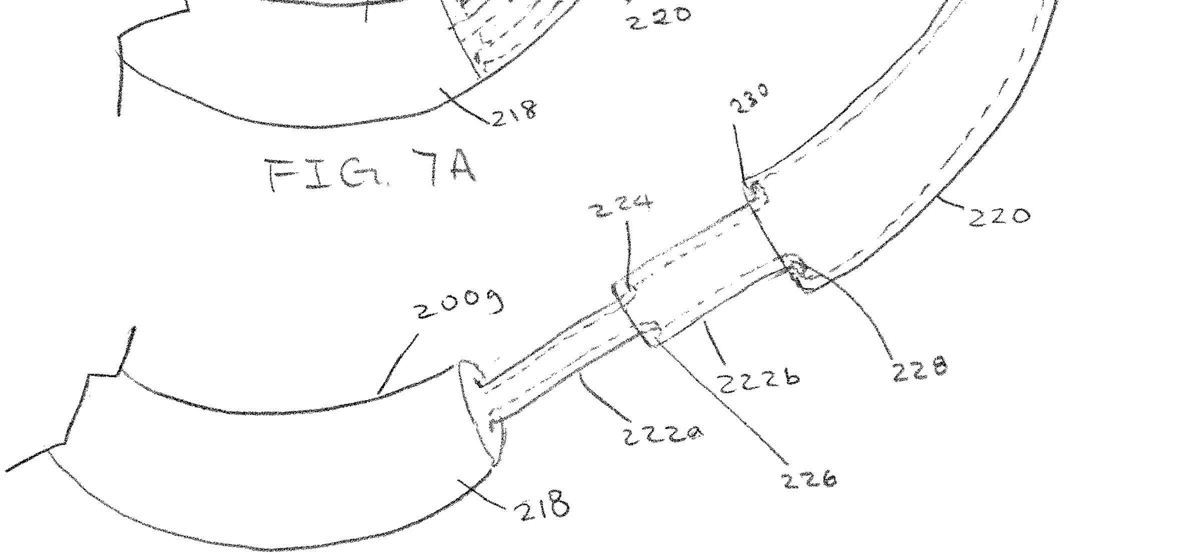
Figure 7C:
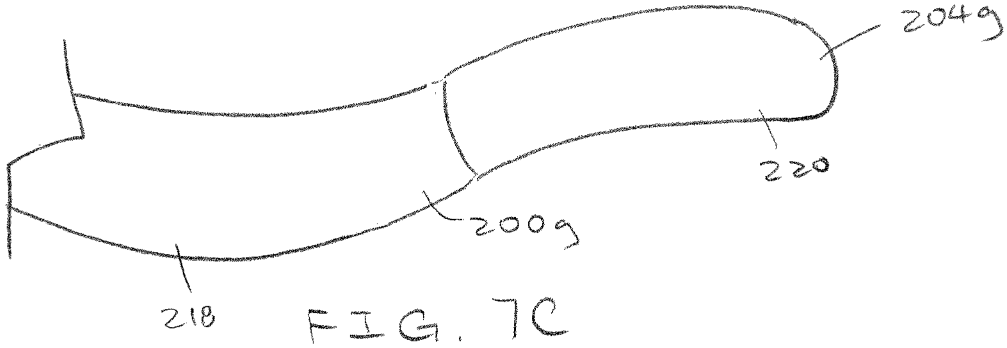

FIGS. 7A-7C illustrate a tentacle/dildo 200*g* with telescopic and rotatable features. Dildo 200*g* has a support portion 218 at the proximal end 208 and an extendable portion 220 at the distal end 204. The extendable portion 220 is substantially hollow to house a plurality of tubular elements 222*a* and 222*b* that are nested and stored therein when the extendable portion 220 is in a collapsed position as shown in FIG. 7A. When extendable portion 220 is in an extended position as shown in FIG. 7B, tubular elements 222*a* and 222*b* are extended and exposed. Tubular element 222*a* is fixedly attached to the support portion 218 with its distal end having an outwardly extending flange 224. Tubular element 222*b* has a larger diameter than tubular element 222*a* with an internal rim 226 that engages outwardly extending flange 224. The distal end of the tubular element 222*b* has an outwardly extending flange 228 that engages an internal rim 230 at the hollow end of the extendable portion 220. The corresponding flange 224-rim 226 and flange 228-rim 230 engagements may be click-lockable at full extension of the tentacle/dildo 200*g* to prevent collapsing and/or rotation of the extendable portion 220. Similarly, when the tentacle/dildo 200*g* is in a collapsed position, it may be click-lockable to prevent unintended extension of the extendable portion 220. Other locking means known to one skilled in the art can also be used, such as twist-lock, detent-hole, bayonet mount, latch, etc. The extendable portion 220 may be rotatable relative to the support portion 218 such that the overall curved body of the tentacle/dildo 200*g* can vary with the distal end 204*g* pointing at different rotational angles.

Figure 8A:
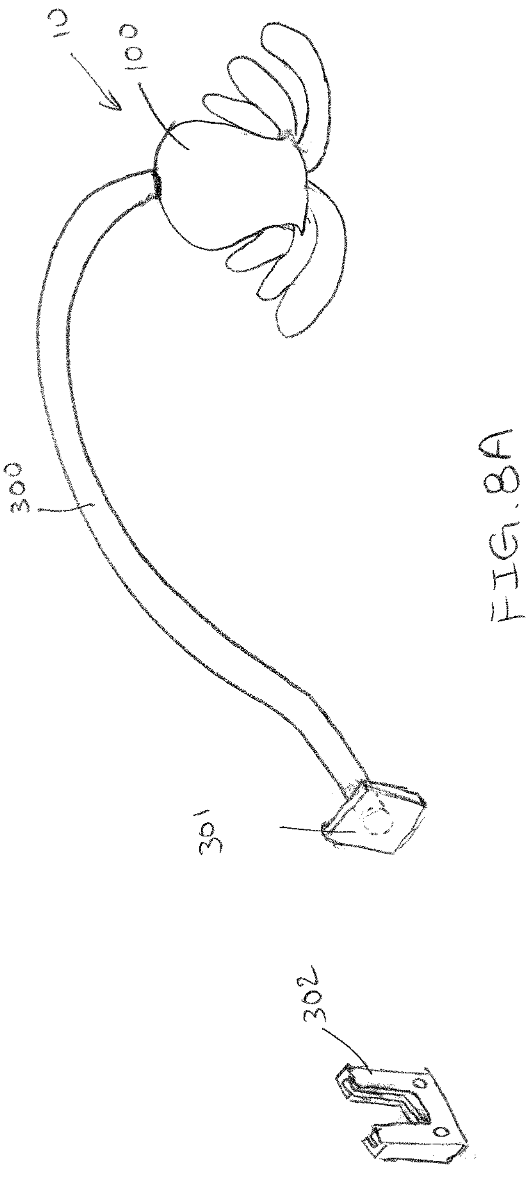
FIGS. 8A and 8B illustrate different methods of mounting the sexual stimulation device of the present invention.
Figure 8B:
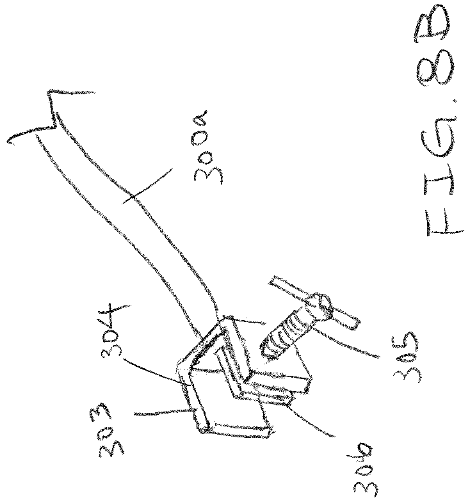

FIGS. 8A and 8B illustrate two different, optional, methods of mounting the sexual stimulation device 10. FIG. 8A shows a curved arm extension 300 with one end attached to the mantel base 100 of the sexual stimulation device 10 and the other end has a mating plate 301 that is removably mountable to a bracket 302. Bracket 302 can be fixedly positioned on a wall, a bed frame, or a sturdy support with fastening element(s) such as screw, bolt, etc. Bracket 302 matingly receives mating plate 301 by sliding the mating plate 301 into the slots of the bracket 302. A locking feature known to one skilled in the art may be provided for the bracket 302 or the mating plate 301 to prevent accidental dislodgement of the mating plate 301 from the bracket 302. Although the arm extension 300 is shown to be fixedly attached to the mantel base 100 and the mating plate 301, they can also be removably attached by means known to one skilled in the art such that the arm extension 300 can be stored separately from the sexual stimulation device 10. The curved arm extension 300 can also be rotatably and pivotably attached to the mantel base 100 to allow rotational and pivoting movements of the sexual stimulation device 10 for the convenience and comfort of the user.

FIG. 8B shows a curved arm extension 300*a* with the one end having a clamp element 303. The clamp element 303 includes a frame 304 and a movable jaw 306 that is attached to a screw handle 305. The clamp element 303 allows the sexual stimulation device 10 to be mounted directly to a bed frame or a sturdy support. Upon clockwise rotation of the screw handle 305, jaw 306 moves towards the frame 304 to sandwich a portion of the bed frame therebetween to secure the clamp element 303 on the bed frame. Counter-clockwise rotation of the screw handle 305 moves the jaw 306 away from the frame 304 to release the clamp element 303.

It is intended that the sexual stimulation device 10 of the present invention has multiple tentacles 200 with each tentacle 200 having a different shape, size, color, texture, feature, or made of different material to satisfy the diverse interests or needs of the user. Additional tentacles 200 with different features may be purchased and interchangeably attached to the mantel base 100. The removability of the tentacle 200 from the mantel base 100 advantageously allows it to be used independently from the mantel base 100 if desired and allows attachment of as many (or as little) tentacles 200 on anywhere on the mantel base 100, at a time, as desired by the user.

The features of the invention illustrated and described herein are the preferred embodiments. Therefore, it is understood that the specification is intended to cover unforeseeable embodiments with insubstantial differences that are within the spirit of the specification.

What I claim is:

1. A sexual stimulation device comprising:

a base having an upper portion and a lower portion; and a plurality of phallic elements attached to said lower portion of said base;

wherein each said phallic element has a body with a distal end pointing in a generally upward direction.

2. The sexual stimulation device of claim 1 wherein at least one of said plurality of phallic elements is fixedly attached to said lower portion of said base.

3. The sexual stimulation device of claim 1 wherein at least one of said plurality of phallic elements is removably attached to said lower portion of said base.

4. The sexual stimulation device of claim 1 wherein at least one of said plurality of phallic elements is movable relative to said base.

5. The sexual stimulation device of claim 1 wherein at least one of said plurality of phallic elements is rotatable relative to said base.

6. The sexual stimulation device of claim 1 wherein at least one of said plurality of phallic elements is telescopically extendable relative to said base.

7. The sexual stimulation device of claim 1 wherein said upper portion is bulbous and said lower portion is concave, said lower portion comprises a track on said lower concave portion, and said plurality of phallic elements are movably attached to said track and positionable anywhere on said track.

8. The sexual stimulation device of claim 7 wherein said track is circular.

9. The sexual stimulation device of claim 1 wherein said plurality of phallic elements are not evenly spaced apart from each other.

10. The sexual stimulation device of claim 1 wherein said at least one of said phallic elements has a curved body.

11. The sexual stimulation device of claim 1 further comprising means for removable attachment of at least one of said plurality of phallic elements to said base.

12. The sexual stimulation device of claim 11 wherein said removable attachment means comprises:

a hole near a proximal end of said at least one of said plurality of phallic elements;

a cavity at the proximal end of said at least one of said plurality of phallic elements;

a mounting element at said lower portion of said base having a spring-loaded detent that correspondingly fits into said hole upon mating engagement of said cavity to said mounting element.

13. The sexual stimulation device of claim 11 wherein said removable attachment means comprises:

an internal thread at a proximal end of said at least one of said plurality of phallic element;

a mounting element at said lower portion of said base having an external thread that correspondingly engages said internal thread.

14. The sexual stimulation device of claim 1 wherein each of said plurality of phallic elements is different in shape, size, color, texture, material, or feature.

15. The sexual stimulation device of claim 1 wherein one of said plurality of phallic elements has at least one protrusion at a distal end.

16. The sexual stimulation device of claim 1 wherein one of said plurality of phallic elements includes a vibrator.

17. The sexual stimulation device of claim 1 wherein one of said plurality of phallic elements includes a heating element.

18. The sexual stimulation device of claim 1 mountable on a support, further comprises an arm extension having a first end and a second end, said first end is attached to said base, and said second end is adapted to attach to said support.

19. The sexual stimulation device of claim 18 wherein said second end of said arm extension has means for removable attachment to said support.

20. The sexual stimulation device of claim 19 wherein said removable attachment means comprises a clamp element.

* * * * *